(12) United States Patent
Hernan Izquierdo et al.

(10) Patent No.: US 9,615,570 B2
(45) Date of Patent: Apr. 11, 2017

(54) METHOD OF FREEZING CELLS

(71) Applicant: Cellulis, S.L., Santona (Cantabria) (ES)

(72) Inventors: Roberto Hernan Izquierdo, Santona (ES); Natalia Gallot Escobal, Santona (ES); Antonio Cruz Pacheco, Santona (ES)

(73) Assignee: Cellulis, S.L., Santona-Cantabria (ES)

( * ) Notice: Subject to any disclaimer, the term of this patent is extended or adjusted under 35 U.S.C. 154(b) by 0 days.

(21) Appl. No.: 14/487,686

(22) Filed: Sep. 16, 2014

(65) Prior Publication Data

US 2015/0140656 A1   May 21, 2015

Related U.S. Application Data

(60) Provisional application No. 61/906,640, filed on Nov. 20, 2013.

(51) Int. Cl.
*A01N 1/02* (2006.01)
*C12M 1/00* (2006.01)

(52) U.S. Cl.
CPC ......... *A01N 1/0221* (2013.01); *A01N 1/0284* (2013.01); *C12M 45/22* (2013.01)

(58) Field of Classification Search
CPC .................................................. A01N 1/0221
See application file for complete search history.

(56) References Cited

U.S. PATENT DOCUMENTS

| | | | |
|---|---|---|---|
| 3,257,072 A * | 6/1966 | Reynolds | A61M 1/029 137/255 |
| 5,863,715 A | 1/1999 | Rajotte et al. | |
| 6,596,531 B2 | 7/2003 | Campbell et al. | |
| 7,341,829 B2 | 3/2008 | Scholl et al. | |
| 2005/0106554 A1 | 5/2005 | Palecek et al. | |
| 2006/0019233 A1 | 1/2006 | Yaghmour | |
| 2008/0092560 A1 | 4/2008 | Loa | |
| 2009/0170059 A1 | 7/2009 | Klingemann | |
| 2010/0297600 A1 | 11/2010 | Cecchi | |
| 2014/0004500 A1 | 1/2014 | Hernan Izquierdo et al. | |

FOREIGN PATENT DOCUMENTS

| | | |
|---|---|---|
| EP | 1869976 | 12/2007 |
| JP | 2069200 | 3/1990 |
| JP | 2002253205 | 9/2002 |

OTHER PUBLICATIONS

Draper et al. Journal of Visulized Experiments, 2009, pp. 1-4.*
Armitage, WJ, Freezing Monolayers of Cells Without Gap Junctions, Cryobiology, Apr. 2003, pp. 194-196, 46(2), Bristol, U.K.
Liu, B., et al., Effects of Two-Step Freezing on the Ultra-Structural Components of Murine Osteoblast Cultures, Cryo Letters, Nov.-Dec. 2006, pp. 369-374, 27(6), Shanghai, China.
Acker, JP, et al., Intercellular Ice Propagation: Experimental Evidence for Ice Growth through Membrane Pores, Biophys J., Sep. 2001, pp. 1389-1397, 81(3), Edmonton, Canada.
Ware, et al., Controlled-rate freezing of human ES cells, Biotechniques, Jun. 2005, pp. 879-883, 38.
Calmels, et al., Preclinical evaluation of an automated closed fluid management device: Cytomate, for washing out DMSO from hematopoietic stem cell grafts after thawing, Bone Marrow Transplant, May 2003, pp. 823-828, 31(9).
Falkow, et al., The Prokaryotes, 2006, Bacteria: Firmicutes, Cyanobacteria.
Chang, et al., Changes in membrane structure induced by electroporation as revealed by rapid-freezing electron microscopy, Biophys. J., Jul. 1990, pp. 1-12, 58.

* cited by examiner

*Primary Examiner* — Bin Shen
(74) *Attorney, Agent, or Firm* — Timothy J. Monahan; Monahan & Company, LLC

(57) ABSTRACT

The present invention is a method of freezing cells comprising the steps of incubating said cells in a solution comprising a cryoprotective agent, concentrating the cells resulting from the previous step withdrawing the eluent essentially free of cells, and freezing the resulting concentrated cells. The cells frozen by the invention's method render a high post-thawing viability, reduce cryoprotectant related toxic events and promote cells life in a suspension state after thawing. The invention also comprises the container comprising the frozen cells.

31 Claims, 11 Drawing Sheets

MDCK cells

MDCK cells

CHO cells

CHO cells

D

A          B

A  B  C  D

Appendix B

METHOD OF FREEZING CELLS

CROSS REFERENCE TO RELATED APPLICATION

This application claims the priority of U.S. Provisional Application No. 61/906,640 filed on Nov. 20, 2013, which is incorporated herein by reference.

FIELD OF THE INVENTION

The invention discloses a method of freezing highly-compacted cells that increases the viability and functionality of thawed cells. The method eases the inoculation of bioreactors with large amounts of cells in a small space, and is also useful in basic research and cell therapy applications in the biotechnology and biopharmaceutical field.

BACKGROUND ART

Cryopreservation is the most common approach for long term cell storage. The critical step for cryopreservation is the addition of the cryoprotective agents, such as dimethyl sulphoxide (DMSO) or glycerol and most of them toxic for the thawed cells. Most slow-cooling protocols accept as gold standard the use of 5 to 15% of DMSO for cryoprotectant agent and a controlled freezing temperature at a cooling rate of 1° C. per minute in order to avoid ice crystals formation that would damage the cells. Another alternative to minimize cryodamage is to avoid ice crystallization through the use of vitrification protocols, wherein the temperature is rapidly decreased to vapour or liquid phase of liquid nitrogen.

Cryoprotective agents do protect by modifying the freezing behavior of cells, specifically affecting the rates of water transport and ice crystal formation across the cell membrane.

For successful cryopreservation of most cell types a homogeneous cooling rate through the whole sample is crucial. Large volumes of cryopreservation solutions are subjected to temperature gradients that lead to non-homogeneous cooling rates. Routine procedures usually involve slow cooling, typically at a controlled freezing rate of 1 to 2° C./min. This is always followed by rapid thawing.

To freeze a large volume of cells, the dimensions of the package are also important. Ice crystallization is a strongly exothermic event, so freezing a large volume of an aqueous cell suspension involves the removal of a large quantity of heat energy. The rate at which heat is removed from the cell suspension as it is frozen will therefore be a large factor in determining how rapidly ice can form. If heat removal is inefficient, the temperature in the center of volume may reach a plateau close to the melting temperature of ice in the solution. For a large package, this would cause a substantial differentiation in cell environment across the sample during freezing, as the freezing profile at the surface would be quite different from that at the center (Avis K E & Wagner C M, 1999, Cryopreservation Applications in Pharmaceuticals and Biotechnology. Drug Manufacturing Technology Series, Volume 5, p-181-313: Interpharm Press).

U.S. Pat. No. 5,863,715 A tries to tackle this problem using a flexible container, a freezer bag holder that maintains the cross-sectional area small enough to allow a uniform heat transfer throughout all regions of the said bag. Drawbacks to this method include the need for a large storage space for such amount of cells, implying extra costs. Additionally, cryobags may also break off during handling and storage at very low temperatures.

US 2006019233 teaches how to reduce the freezing solution volume by concentrating at densities between $3 \times 10^7$ and $5 \times 10^8$ blood cells per ml, increasing in turn the rate of DMSO. Drawbacks of the method are thus related with the toxic characteristics of the cryogenic agent rendering cell viability limitations ranging from 60 to 90%, and also cell density limitations for particular cell types such as non-blood related cells. This method teaches away from the present invention, as the latter removes the excess of cryogenic agent in order to diminish its rate per cell in the freezing vial.

Some cell types are more sensitive to cryopreservation, showing very poor survival rates. Ware reported that increasing the liquid volume in the vial from 0.25 ml to 1 ml reduces cell survival to roughly 25% (Ware et al, "Controlled-rate freezing of human ES cells". Biotechniques 38, 879-883 June 2005). Ware concluded that loss of efficiency is associated to the slower thaw rates of large-volume containers than those of smaller volumes container, i.e. vials versus straws. A rapid thaw was found to be critical for a successful cryopreservation.

Some basic thawing conditions are established in the art as current standard protocols for the best recovery of the cells. These protocols include temperature optimization and dilution of the cryoprotectant solution right after thawing by adding fresh cell culture medium for the recovery of the cells in an appropriate osmotic environment. As an alternative, the cryoprotective agent can be removed. The reconstitution steps involved in these procedures can provoke cell damage due to swelling when eluting the cryoprotective agent. In order to solve this problem, the present invention is able to keep an optimal cryoprotectant percentage and cell concentration ratio in the freezing solution during the equilibration time. The cryoprotectant agent enters the cells in an amount enough to be effective, the excess thereof is however left out in the medium and removed just before freezing. Later, the progressive dilution at thawing will greatly soften the cellular osmotic shock.

In order to avoid exposure of the cells and to preserve sterility, several proposals are described in the art. These comprise devices such as Ensura-Sep™ that uses a single centrifugation step using proprietary canisters, or more sophisticated and expensive solutions such as Cytomate cell processing system from Baxter (Calmels et al, "Preclinical evaluation of an automated closed fluid management device: Cytomate, for washing out DMSO from hematopoietic stem cell grafts after thawing" Bone Marrow Transplant. 2003 May; 31(9):823-8.) or the Sepax® system (Rodriguez L. et al, "Washing of cord blood grafts after thawing: high cell recovery using an automated and closed system." Vox Sang 2004 October; 87(3):165-72) wherein cells are transferred from bag to bag in enclosed systems.

EP 2471359 A1 teaches a method that avoids the need of incorporating new fresh medium to the thawed cells for the dilution of the cryoprotective agent in high throughput microplate vessels. This is achieved by the previous freezing of an extra layer of culture medium in addition to the frozen cell solution. Although this method offers a lack of manipulation and increases cell viability after thawing due to the minimization of the osmotic shock, the amount of cells to be frozen remains restricted.

The problem of the art is then to provide a cryopreservation method of higher cell viability rates after thawing, suitable for large amount of cells. The solution provided by the present invention is to perform a concentration step after or during the equilibration of the cells with the cryoprotectant agent, minimizing the rate of the latter in the freezing solution, which increases viability in a surprising degree. Further, the freezing of these concentrated cells in a high surface to volume ratio allows a more homogeneous cooling and thawing rate that will optimize viability rates.

DESCRIPTION OF THE INVENTION

The present invention is a method of freezing cells comprising:
a) to incubate said cells in a solution, preferably at a temperature range of 3 to 5° C., said solution comprising a cryoprotective agent,
b) to concentrate the cells resulting from the previous step, withdrawing the resulting eluent essentially free of cells, and
c) to freeze the resulting concentrated cells.

Pending on the desired final concentration, a preferable aspect of the method of the invention comprises an intermediate step of re-suspending the concentrated cells prior to freezing.

In the scope of the present application, to "concentrate" the cells means to obtain a higher number of cells per milliliter than the standard concentration within the freezing medium. This rate is not fixed, and varies from one cell type to another. In adherent mammalian nucleated cells, for example, this standard concentration of cells may vary between 0.5 M/ml to 10 M/ml depending on the cell type, typically between 1 and 5 M/ml. (Ed. F. P. Simione and E. M. Brown. 1991. ATCC Preservation Methods: Freezing and Freeze Drying. American Type Culture Collection, Rockville, Md.). The present invention would allow cryopreservation of 10 M/ml up to 400 M/ml of mammalian adherent cells, pending on the intrinsic cellular volume of each cell type. The maximum concentration possible under the scope of this invention is tied to the size of a pellet formed after centrifugation.

In the scope of the present application, the term "to incubate" is defined as to maintain the cells in a desired solution for a concrete period of time.

The time taken for concentrating the cells can be considered an incubation by itself in addition to the previous incubation. Overall incubation considering steps a) and b) is dependent on the cell type, and varies between 3 and 15 minutes, typically 10 minutes.

At the concentration step the cells can start to cool down. Thus, in a preferred aspect of the invention the concentration step is performed at a temperature cooling gradient range of 1 to 2° C./min. In another preferred aspect, concentrating is performed by centrifugation or filtration techniques.

In the scope of the present application, the expression "to freeze" means to decrease the temperature of the liquid eluent or cell solution below their respective freezing point temperature to form a frozen body. In a preferred aspect of the method of the invention, the freezing of the cells is performed at a temperature cooling gradient range of 1 to 2° C./min. In another preferred aspect, it is performed by vitrification.

In the scope of the present invention, the term "vitrification" is defined as a rapid cooling of the cell solution through the glass transition temperature, at the so called "flash freezing" directly in vapor or liquid phase of nitrogen. The rapid freezing typically reaches down to −130° C. or −196° C.

The cryoprotective agent should be present at a suitable concentration, this understood as the effective concentration at which a particular cell type shows the highest viability. The concentration of cryoprotectant medium during the incubation is conditioned by the cell rate in solution prior concentrating.

In a preferred aspect, said cryoprotective agent is selected from the group consisting of DMSO, glycerol, polyvinylpyrrolidone, ethylene glycol, methanol, methyl acetamide and sugars, or a combination thereof, most preferably DMSO. The concentration typically used of DMSO is of between 5 to 20% in volume with respect to the total volume of the solution. The incubation or equilibration phase allows the correct internalization of the cryoprotectant inside the cells. The permeating cryoprotectant enters the cell replacing intracellular water. Higher cell concentrations reduce the amount of cryoprotectant per cell; however, the increase of cell concentration in the freezing solution would result in a reduced post-thaw recovery. The aim of the present invention is to reach a complete equilibration of the cells with the cryoprotectant by the withdrawal of the excess of same that was not internalized within the cells.

The cells frozen by the invention's method render a high post-thawing viability, reduce cryoprotectant related toxic events and promote cells life in a suspension state after thawing.

In the scope of the present application, the term "equilibration" refers to the time that is required by the cells in contact with permeable cryoprotectants in order to equilibrate intercellular solutes before freezing.

In a preferred aspect of the invention, the cells to be frozen are bacteria, plant cells or animal cells. Said animal cells are preferably selected from the group consisting of blood cells, stem cells, induced pluripotent stem cells, tumor cell lines, immortalized cell lines, continuous cell lines, genetically modified cell lines, hybridomas, primary isolated cells, embryos, sperm and oocytes. Even more preferably, said stem cells are selected from the group consisting of embryonic stem cells, adult stem cells, tissue specific stem cells, mesenchymal stem cells, hematopoietic stem cells and progenitor cells.

In the scope of the present invention, the term "stem cells" refers to those cells that own the ability to go through numerous cell division cycles while maintaining the undifferentiated state, and at the same time are pluripotent able to differentiate into specialized cell types.

In the scope of the present invention, the term "tumor cell lines" refers to permanently established cell culture lines originated from in vivo tumors.

In the scope of the present invention, the term "immortalized cell lines" refers to those lines of cells genetically engineered to reproduce themselves indefinitely.

In the scope of the present invention, the term "continuous cell lines" refers to those lines of cells that are able to reproduce in vitro indefinitely.

In the scope of the present invention, the term "genetically modified cell lines" refers to those cells lines whose genetic material has been modified or altered, typically through genetic engineering techniques.

In the scope of the present invention, the term "induced pluripotent stem cells" refers to those cells that derive from adult somatic non-pluripotent cells, and have been genetically reprogrammed to lose their tissue-specific qualities and become pluripotent.

In a preferred aspect of the invention, the freezing of step c) is performed in a receptacle of a surface-to-volume ratio between 6 and 50 $cm^{-1}$, more preferably a ratio of between 8 and 21 $cm^{-1}$. The small volume of cells to cryopreserve in addition to the high surface-to-volume ratio allows a homogeneous cooling rate for all cells. The heat transfer occurs faster through the cells when they are concentrated and exposed to an external temperature source in a high surface area to volume ratio than by the freezing methods used in the art (i.e. Cryovial). This less temperature gradient provides a more homogenous freezing process as well as faster thawing time for all cells, resulting in a more efficient cell resuscitation. Increasing the surface area to volume ratio considerably reduces the temperature gradient and heat transfer.

Thus, another preferred aspect is the container comprising the frozen cells according to the method of the invention.

In a particular aspect of the invention, this container is a bottle with a conical lid, containing a frozen pellet of cells in said lid and frozen fresh biologically acceptable eluent in the recipient. In this case, the cells had been concentrated in an upside down position, collecting a cell pellet on the lid of the bottle. After centrifugation, the recipient containing the resulting eluent essentially free of cells is replaced by another recipient containing fresh eluent. This renders a closed bottle containing fresh diluting solution and a cell pellet in the lid, which are frozen at the same time (FIG. 15).

In another particular aspect of the invention, the container is a clamped bag containing the frozen concentrated cells at a lower side and frozen fresh biologically acceptable eluent at an upper side of the bag. In this case and after centrifugation, the bag is clamped above the concentrated cells compressing the two walls of the bag. The resulting eluting medium free of cells is discarded. Then, fresh eluent medium is introduced in the bag while the cells are still confined by the clamp compression. Both the eluent solution and the cells are frozen at the same time. Upon thawing, the clamping is removed and both solutions merge, allowing a gradual and standardized reconstitution of the cells (FIG. 16).

In yet another preferred aspect, the container comprises at least two compartments communicated with each other creating a common space that ends in an opening, wherein one compartment is at least partially filled with a frozen fresh biologically acceptable eluent and another compartment hosts the frozen concentrated cells, having the compartment hosting the cells a surface-to-volume ratio between 6 and 50 $cm^{-1}$ and being placed in the outer side of said container. Placing the concentrated frozen cells in the outer side of the container allows a direct heat transfer thawing approach from an exothermic reaction source. In a more preferred aspect, the volume of the concentrated cells is equal or less than the volume of said liquid eluent.

Compartmentalization can be achieved by a fluid occupying the interface of the cell and eluent solutions, by the cell and eluent solutions being two frozen bodies in contact with each other, or by a membrane or a physical rigid wall that keep the eluent and the cell solution unmixed in the liquid state.

The referred compartmentalized container can be a vial, a syringe, a straw, a vessel, a flask, a bag or a dish, more preferable a vial or a flask, and even more preferable a syringe.

The compartmentalized flask of the invention has a flat internal wall separating both compartments. Alternatively, the flask is a rigid cylinder-shaped container with a circular internal wall. Both aspects provide two independent compartments, leaving the cell solution and the eluent physically separated (FIGS. 17-18).

The barrel of the compartmentalized syringe containing the frozen cells of the invention comprises a part A) comprising said two compartments communicated with each other creating a common space and a plunger handle screwed in a first end of said part A) whereas a second end is able to be assembled with a first end of a part B), said part B) comprising a piston, said piston having a threaded through hole wherein said plunger handle is able to be screwed, and an orifice in a second end (FIG. 20-21). In this orifice will typically be inserted a needle.

The eluent used in the present invention is an isotonic solution, a crystalloid solution, a saline solution, a glucose solution, a dextrose solution, a lactate solution, a colloid, hydroxyethyl starch, gelofusine, a DNase solution, benzonase, plasma and serum, or a combination thereof or any other biologically acceptable liquid eluent.

In the scope of the present invention, the term "biologically acceptable eluent" refers to any liquid eluent compatible with cells living in healthy conditions.

The cells frozen in this compact state show additional advantages. The invention's container allows a high standardization of thawing procedures, minimize microbial contamination and need no further processing after thawing expediting the cells for direct treatment to the patient, when needed.

The containers' design of the present invention allows a gradual and standardized reconstitution of the cells upon thawing. The proposed thawing process for the method of the invention can be the immersion of the said container in an upside-down position into a dry heat source at a temperature of 37° C. or higher. The cell solution would be rapidly thawed right before the eluent solution, and both would gradually mix in a single liquid composition, thereby decreasing the cellular osmotic shock. In addition to the achieved high viability, the freezing-thawing process of the invention avoids cell manipulation and contamination risks, minimizes the post-thawing osmotic shock for a high viability rate and high standardization levels, and is able to administer a direct dose to a patient without further manipulation due to a significant reduction in the amount of cryoprotectant compared to current standards, minimizing undesired side effects, among others.

In addition, the method of the invention prolongs the life of cells in a suspension state after thawing so that thawed cells can be successfully stored at 4° C. within the container for later use, achieving post-thawing survival rates higher than 90%.

The most preferred aspect of the invention is a method of freezing animal cells comprising to incubate said cells in a solution comprising DMSO at a temperature of 4° C., to concentrate the cells resulting from the previous step withdrawing the eluent essentially free of cells, and to freeze the resulting concentrated cells at a cooling gradient range of 1 to 2° C./min in a compartment with a surface-to-volume ratio between 8 and 21 $cm^{-1}$, of a flask, said flask having another compartment hosting the complete cell culture medium, wherein said two compartments communicate to each other creating a common space at the top.

Still another preferred aspect of the invention is the container itself, this container comprising at least two compartments communicated with each other creating a common space that ends in an opening, wherein one of said compartments placed in the outer side has a surface-to-volume ratio of between 8 and 21 $cm^{-1}$. In more preferred aspect, said container comprises a removable lid in said opening and is preferably a vial or a flask. In another preferred aspect, the container comprises a needle coupled to said opening, and is preferably a syringe. Indeed in a more preferred aspect, the barrel of said syringe comprises a part A) comprising said two compartments communicated with each other creating a common space and a plunger handle screwed in a first end of said part A), whereas a second end is able to be assembled with a first end of a part B), said part B) comprising a piston, said piston having a threaded through hole wherein said plunger handle is able to be screwed, and an orifice in a second end. In this orifice will typically be inserted a needle. Even more preferably, the assembly of parts A) and B) of the barrel is performed by a screw.

The process of filling the syringe would comprise filling part A, wherein cells and eluent are placed in the outer and inner compartments respectively; At this point, parts A and B of the syringe could be assembled with the orifice for the needle upwards, and left ready to be frozen. Once frozen, the prefilled syringe must be thawed in a position leaving the orifice for the needle downwards, in order to mix the cells and the eluent gradually along with thawing. Both liquids would fall by gravity through the piston hole and converge in part B. Finally, the piston hole is sealed by screwing the plunger handle into it and the syringe is then ready to use.

The plunger handle optionally comprises one or two screws. In the case of one screw, this will be originally inserted in one end of part A) of the syringe, leaving the whole body of said plunger handle outside the syringe. In the case that the plunger handle has two screws, one at the top and another one in the body, the screw of the body will be inserted in one end of part A), whereas the screw of the top will be inside the space of the barrel with the aim of being screwed in the piston at the time of use.

DETAILED DESCRIPTION OF PARTICULAR ASPECTS

Figure 1:
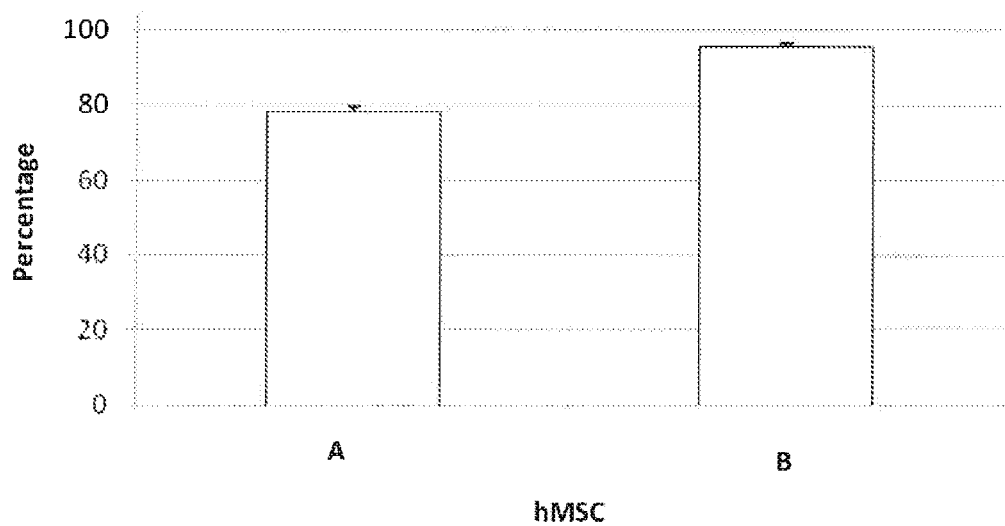
FIG. 1: Post thawing membrane integrity (Trypan Blue) for human Mesenchymal Stem Cells hMSC. A: Gold Standard method. B: Invention's method.

The following examples are provided in order to demonstrate and further illustrate certain preferred aspects, however not to be construed as limiting the scope of the present invention. The referenced gold standard freezing protocol is the most commonly used method of the art for most cells types, yielding the highest percentages of viable cells achieved (Ed. F. P. Simione and E. M. Brown. 1991. ATCC Preservation Methods: Freezing and Freeze Drying. American Type Culture Collection, Rockville, Md.).

EXAMPLES

Example 1

Freezing and Thawing Assay of CHO Cells in a Wet Cell Pellet

The cell line CHO was acquired from the Heath Protection Agency (HPA). Cells were cultured in flasks (Nunc, Thermo Scientific) in complete culture medium (DMEM/Nutrient mixture F12 Ham from Sigma Aldrich, supplemented with 10% FBS from Gibco, 100 µg/ml penicillin and 100 IU/ml streptomycin from Hyclone), grown until they were 80% confluent and then harvested. Cell detachment was achieved by incubation with 4 mM PBS-EDTA (Sigma) at 37° C. for 5 minutes. A total of $30 \times 10^6$ cells were centrifuged at 450×G for 5 minutes. After supernatant removal, cells were suspended in freezing solution (complete culture medium plus 10% DMSO from Sigma) at 4° C. at a density of 3 million cells/ml, and were allowed to equilibrate for 5 minutes at 4° C. Cell densities were determined using an automatic cell counter (Countess®, Invitrogen). One milliliter of this sample of 10 ml was then transferred to a standard cryovial (Nunc®, Thermo Scientific) and freeze down to −80° C. at a rate of 1° C./minute. The remaining 9 ml were centrifuged at 450×G for 5 minutes at 0° C. The supernatant was then completely removed and the wet cell pellet consisting of $27 \times 10^6$ cells at a concentration of $300 \times 10^6$ cells/ml was frozen down to −80° C. at a rate of 1° C./minute. Freezing rates of 1° C./minute were reached by using CoolCell® system (Biocision LLC, California). One week after freezing, both vials were thawed. The cell pellet was thawed in 40 seconds using a dry heating source consisting of an aluminum sheath at 37° C. that fitted closely to the shape of the freezing container. The pellet was then gradually diluted at a pace of 1 ml/minute with 5 ml of complete culture medium contributing to a low osmotic shock. The cells frozen following the gold standard freezing method in the Nunc® vial at a concentration of 3M cells/ml were thawed in a 37° C. water bath. These cells were also gradually diluted at a pace of 1 ml/minute with 5 ml of complete culture medium. Post-thawing cell viabilities were then checked in both assays using Trypan Blue (Countess® cell counter, from Invitrogen). The post-thawing cell viability for both the gold standard freezing method and the invention's frozen cell pellet was 97% and 99% respectively, showing a slight improvement in viability for the new method. One fraction of the diluted cells from the invention's frozen cell pellet was further kept for 1 hour at 4° C. and the viability dropped just 1% (from 99% to 98%) showing the potential for these cells to stay in a stand-by situation after using the invention's freezing method.

Figure 13:
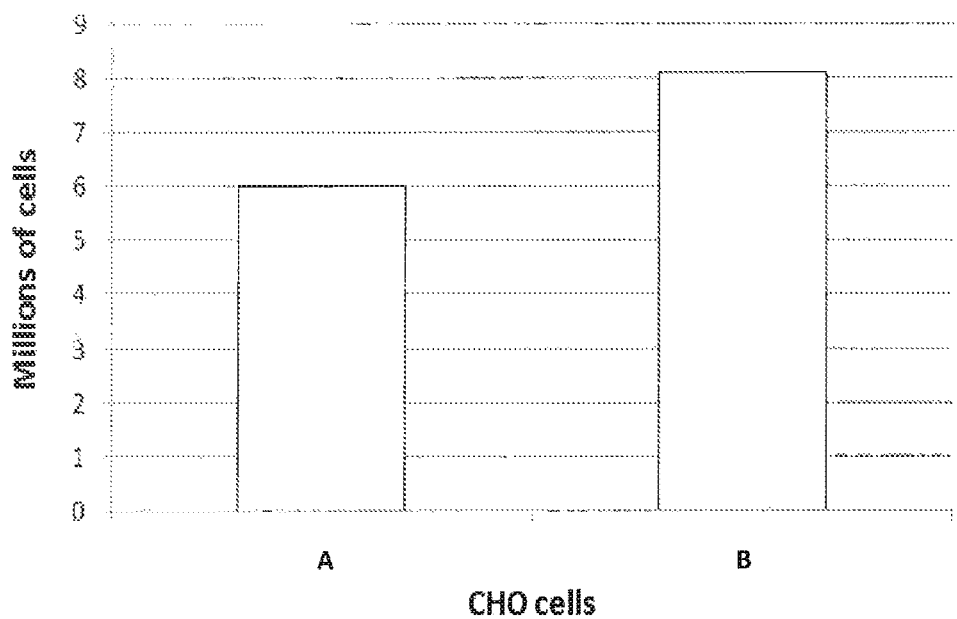
FIG. 13: Total number of CHO cells after 48 hours in vitro culture. A: Gold Standard Freezing Method. B: Invention's frozen pellet method.
Figure 14:
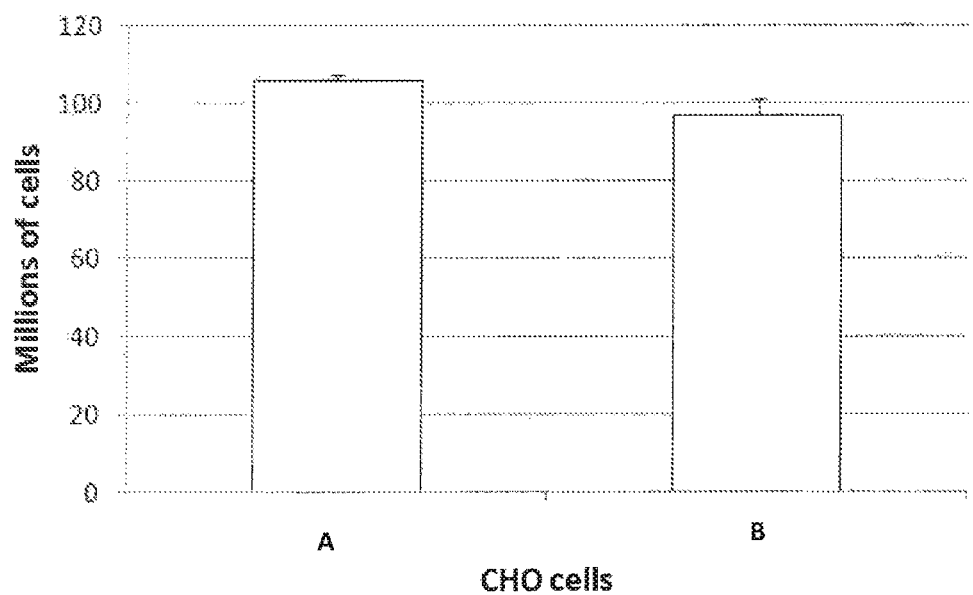
FIG. 14: Total number of CHO cells after 48 hours cell growth. A: Fresh cells. B: cells frozen in a cell pellet.
Figure 15:
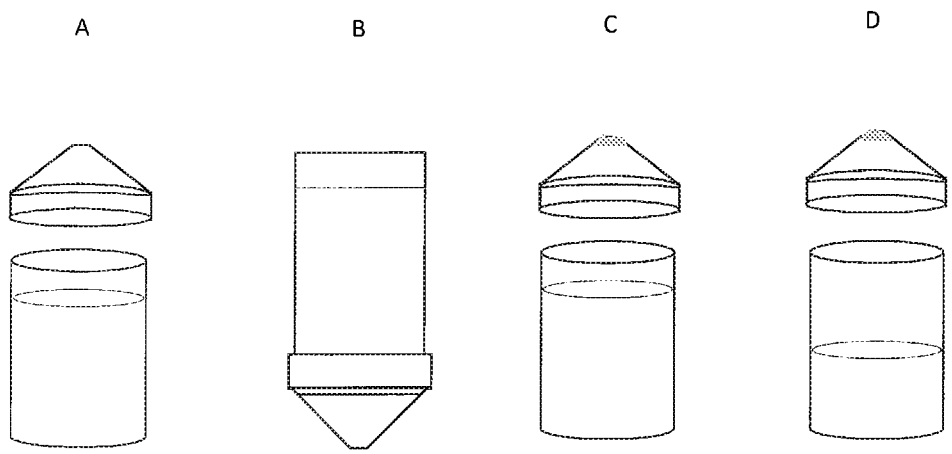
FIG. 15: Freezing bottle of conical lid.
 A. The bottle is filled with a medium containing cells and a cryoprotectant agent.
 B. The bottle is inverted and centrifuged.
 C. The cell pellet is adhered to the lid, and the recipient is discarded.
 D. The recipient is replaced by another recipient with fresh eluent medium, and frozen.
Figure 16:
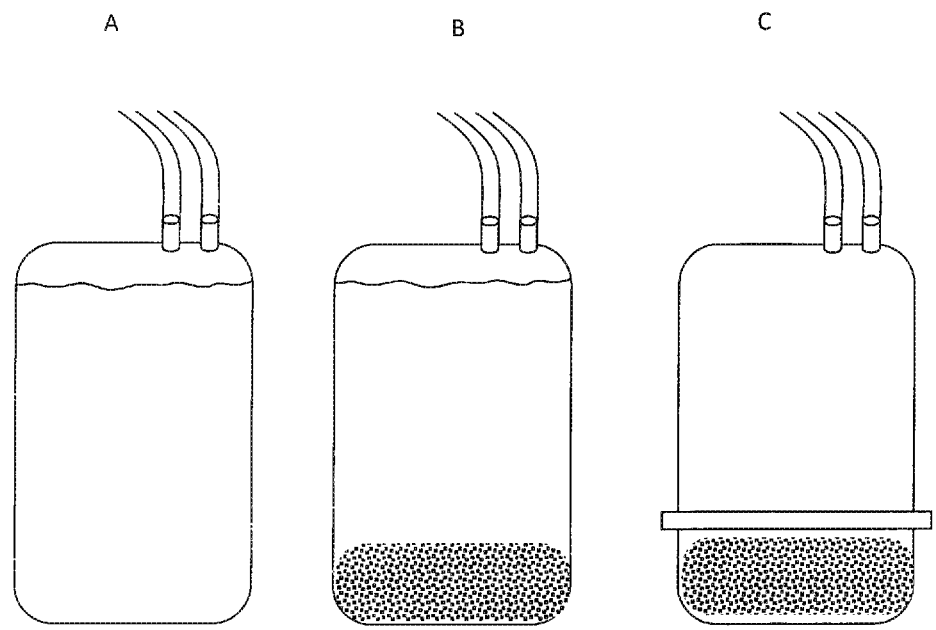
FIG. 16: Freezing clamped bag.
 A. The bag is filled with cells containing cryoprotectant.
 B. The bag is centrifuged and cells are concentrated below.
 C. The bag is clamped above the concentrated cells and the eluent is discarded.
 D. The bag is filled at the top side with fresh eluent medium and both solutions are frozen at the same time.
Figure 16:
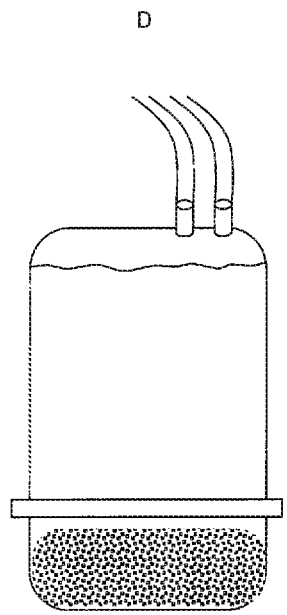
Figure 17:
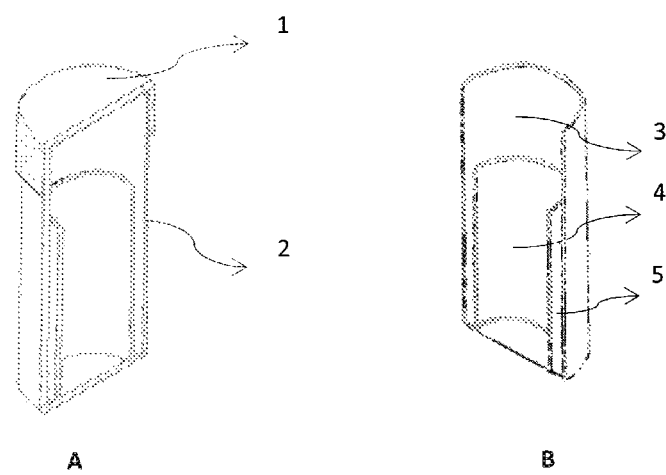
FIG. 17: Freezing container. A: Isometric section view of the freezing container with the lid on. B: Isometric section view of the freezing container showing the inner and outer compartments and the common space at the top.
 1. Lid;
 2. Double wall container;
 3. Common space wherein the liquids get mixed;
 4. Inner compartment;
 5. Outer compartment.
Figure 18:
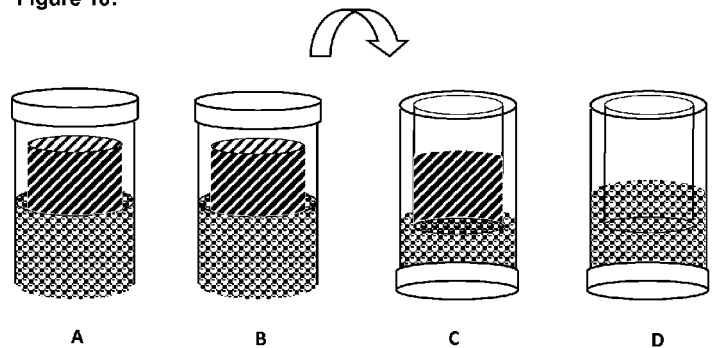
FIG. 18: Different states of the freezing container showing the freezing and thawing processes where the cells and the eluent are frozen in different compartments (A and B) to become mixed at thawing (C and D).
 A. Both compartments are filled with cells and eluent, respectively;
 B. Both liquids are frozen at a controlled temperature;
 C. When the container is heated in an inverted position, the cells solution falls down by gravity prior to the eluent.
 D. The thawing eluent gradually dilutes the freezing solution containing the cells.
Figure 19:
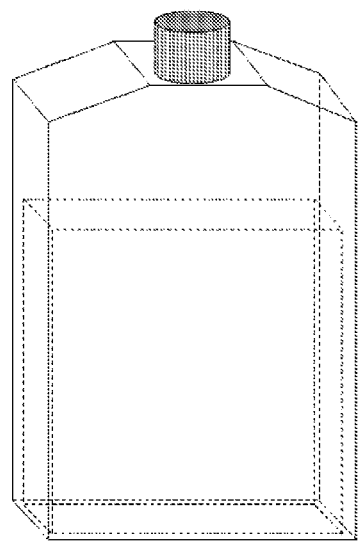
FIG. 19: Isometric view of the flask-shaped freezing container showing the inner and outer compartments separated by a flat internal wall and the common space at the top.
Figure 20:
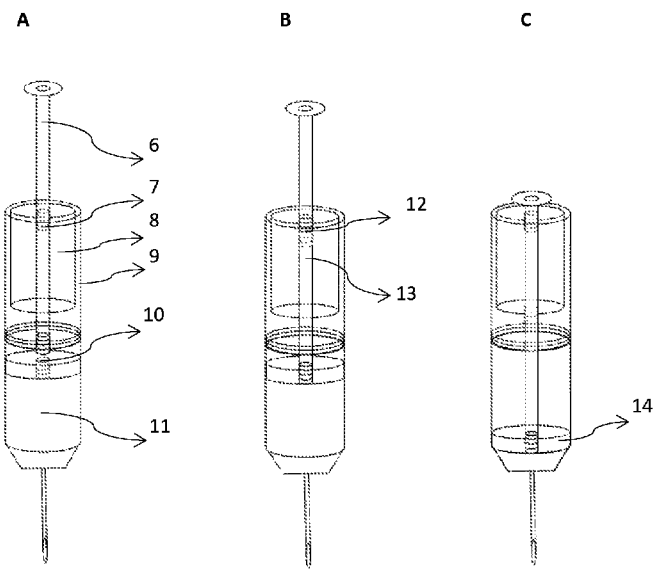
FIG. 20: Isometric view of a prefilled syringe showing the two compartments communicated with each other at the common space wherein both solutions are mixed upon thawing.
 A. The syringe is locked in a prefilled position, wherein the plunger handle (6) is inserted and retained in a female screw at an end of the barrel (7) through a male screw located at a single point on the plunger handle. The inner (8) and outer (9) compartments of the syringe are also shown. The contents of the syringe are thawed in this position and fall by gravity throughout the piston's orifice (10), mixing at the bottom of the syringe (11).
 B. Upon thawing, the syringe's plunger handle (13) is then twisted clockwise until another male screw at the bottom of said plunger handle fits into the threaded orifice of the piston, at the same time that the top male screw of the plunger handle is released from the female screw of the barrel (12). At this position, the air can be expelled from the syringe by pressing on the plunger.
 C. Shows the position of the plunger handle and piston (14) after the content has been expelled.
Figure 21:
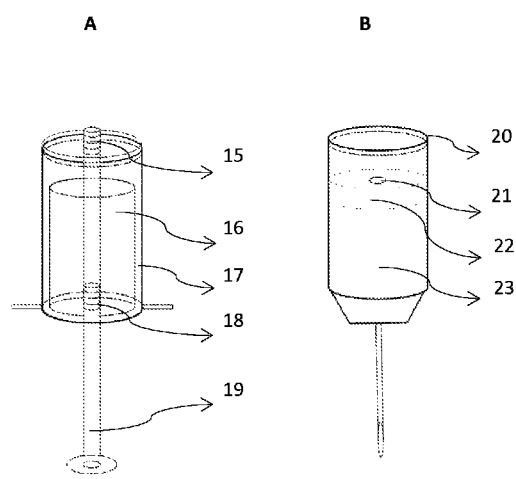
FIG. 21: Assembly of the prefilled syringe in two parts (A and B) prior to filling.
   A. Top part of the syringe ready to be filled with cells and eluent. Includes a screw at the first end (15) and a screw in the body (18) of the plunger handle, the plunger handle itself (19), an the inner (16) and outer (17) compartments of the syringe. This view corresponds well with claimed part A) of the syringe.
   B. Part of the needle of the syringe showing the threaded end (20) for assembling the barrel, the orifice crossing the piston (21), the piston itself (22) and the common space to allocate the thawed liquids (23). This view corresponds well with claimed part B) of the syringe, excluding the needle.

Along with these freezing assays, an identical number of fresh CHO cells from the same batch to that used in the cell pellet freezing assay were seeded in T-175 flasks. In order to compare the post-thawing cell growth recovery between all assays, all cells from both freezing methods and also the fresh cells, were seeded in T-175 flasks, allowed to grow for 48 hours in a $CO_2$ incubator at 37° C. and then the total number of cells was counted using the Countess® cell counter. FIG. 13 shows a clear increment in the number of viable cells after 48 hours culture when comparing the invention's frozen pellet method with the gold standard freezing method ($8.1 \times 10^6$ cells versus $6 \times 10^6$ cells respectively). Further, FIG. 14 shows that there is no significant difference when comparing the 48 hours cell growth between both fresh cells and cells frozen in a cell pellet ($105 \times 10^6$ cells versus $97 \times 10^6$ cells respectively).

Example 2

Freezing/Thawing Assay of Human Mesenchymal Stem Cells (hMSC) Using the Gold Standard Freezing Method and the New Freezing Method Human Mesenchymal Stem Cells (acquired from Millipore) were cultured in flasks in complete culture medium: DMEM low glucose (Hyclone), 2 mM L-glutamine (Sigma), 8 ng/ml bFGF (Millipore), supplemented with 10% FBS inactivated (Gibco), 100 µg/ml penicillin and 100 IU/ml streptomycin (Hyclone). The cells were grown until they were 80% confluent and then harvested. Cell detachment was achieved by incubation with TrypLE™ Express (Invitrogen) for 5 minutes. Cells were centrifuged at 450×G for 5 minutes. After supernatant removal, cells were suspended in 2 ml of freezing solution (CryoStor™ CS5, BioLife Solutions) at 4° C. at a density of 1 million cells/ml and split in two identical halves containing the same number of cells. Cell densities were determined by using an automatic cell counter (Countess®, Invitrogen). Each half was then processed for freezing following two different protocols, the gold standard freezing protocol and the invention freezing protocol. For the gold standard protocol cells were allowed to equilibrate for 10 minutes at 4° C. prior to be frozen down to −80° C. at −1° C./minute in 1.8 ml cryovials (Nunc, Thermo Fisher Scientific). Freezing rates of −1° C./minute were reached by using CoolCell® system (Biocision LLC, California). For the invention method, cells were allowed to equilibrate just for 5 minutes at 4° C. followed by a centrifugation at 450×G for another 5 minutes. During this centrifugation period, the temperature of the freezing solution started to drop at −1° C./minute until reaching 0° C. Cells were then concentrated at a density of 10 Millions of cells/ml and quickly transferred to the compartment of a special freezing container, having said compartment a surface area to volume ratio of 8.4 $cm^{-1}$. Cells were then frozen down to −80° C. at −1° C./min along with an eluent solution that was placed in a separate compartment within said container. All cells from both freezing methods were transferred the next day from −80° C. to −160° C. at the vapour phase of liquid nitrogen.

Figure 2:
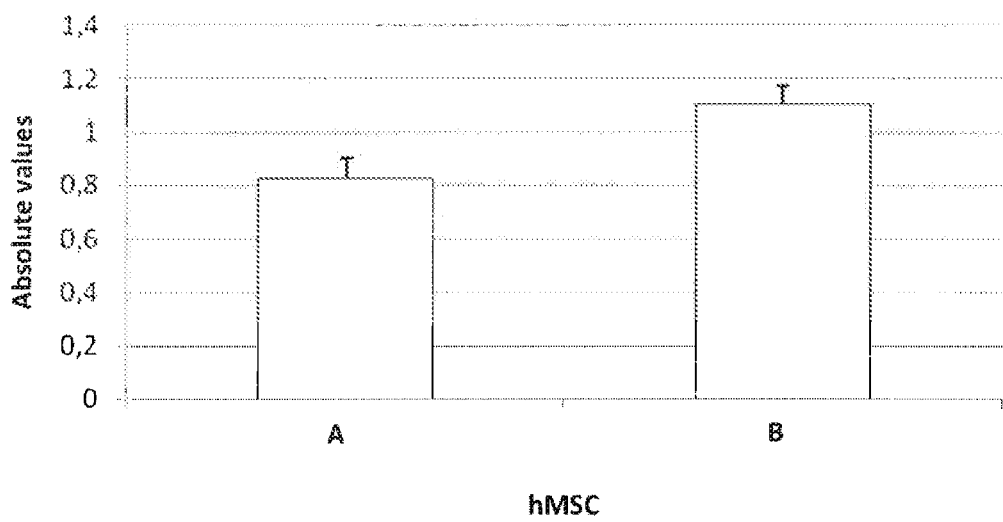
FIG. 2: Viability (Cell Titer-Glo®) 24 h. post-thawing for hMSC. A: Gold Standard method. B: Invention's method.

After one week, the frozen cells of both methods were quickly thawed in a water-bath at 37° C. Thawed cells from the gold standard freezing method were gradually diluted at a pace of 1 ml/minute with complete culture medium. Post-thawing cell viability was then checked and counted in both assays using trypan blue (Countess®, Invitrogen). Cells from both freezing methods were seeded in 96-well plates and metabolic activity was measured after 48 hours in a $CO_2$ incubator at 37° C. to an end point for cell viability using luminescent Cell Titer-Glo® (Promega). Absorbance of the resulting solutions was quantified in a spectrophotometer (Multiskan Ascent, Thermo Labsystems) at 450 nm. The percentage of viable hMSC in terms of cell membrane integrity after the invention's method was 95.5%, whereas at the gold standard method only reached 78.5% (FIG. 1). The cell metabolic activity significantly increased after 24 hours post-thawing at the invention's method compared to the gold standard method (FIG. 2).

Example 3

Vitrification of Mouse Embryonic Stem Cells (mESC)

Mouse Embryonic Stem Cells (acquired from LGC Standards) were cultured in flasks in complete culture medium: DMEM high glucose, 0.1 mM R-mercaptoethanol (Sigma), 10 ng/ml mLIF (Life Technologies), 1% non-essential amino acids (Sigma), supplemented with 20% FBS (Gibco), 100 μg/ml penicillin and 100 IU/ml streptomycin (Hyclone). The cells were grown until they were 80% confluent and then harvested. Cell detachment was achieved by incubation with TrypLE™ Express for 5 minutes. Cells were centrifuged at 450×G for 5 minutes. After supernatant removal, cells were suspended in a freezing medium without DMSO consisting of DMEM high glucose, 10% FBS and 1.25M trehalose (Sigma) and then counted. Cell densities were determined by automatic cell counter. Then, an equal amount of freezing medium containing double concentration (10%) of DMSO was added to give a final DMSO concentration of 5%. The total amount of cells counted was 12 million and the cell concentration in the freezing suspension was 1 million cells per ml. Cells in this final freezing solution were then split in two parts; 0.25 ml were placed in a 1.8 ml Nunc vial (Thermo Scientific) that followed the gold standard protocol, and the remaining 11.75 ml followed the invention's protocol. For the gold standard protocol cells were equilibrated for a total of 10 minutes at 4° C. prior to be flash frozen to −150° C. For the invention's method, cells were allowed to equilibrate just for 5 minutes at 4° C. followed by a centrifugation at 450×G for another 5 minutes. During this centrifugation period, the temperature of the freezing solution started to drop at −1° C./minute until reaching 0° C. Cells were then concentrated at a density of 48 million cells/ml and the resulting 0.25 ml were quickly transferred to a freezing container, having said container a surface area to volume ratio of 20 cm$^{-1}$, allowing a very fast and homogeneous heat transfer. Cells were then flash frozen to −150° C. in the vapour phase of liquid nitrogen.

Figure 3:
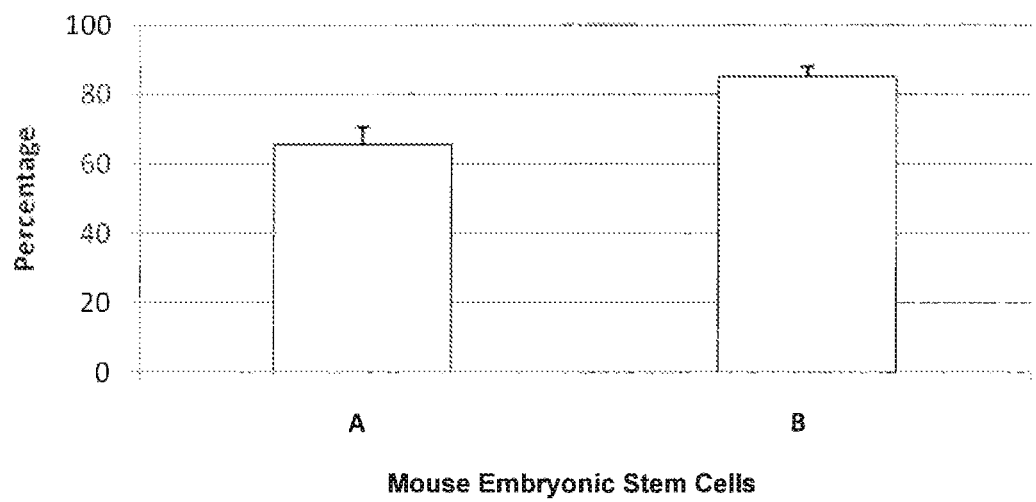
FIG. 3: Post thawing membrane integrity (Trypan Blue) for Mouse Embryonic Stem Cells. A: Gold Standard vitrification method. B: Invention's method.
Figure 4:
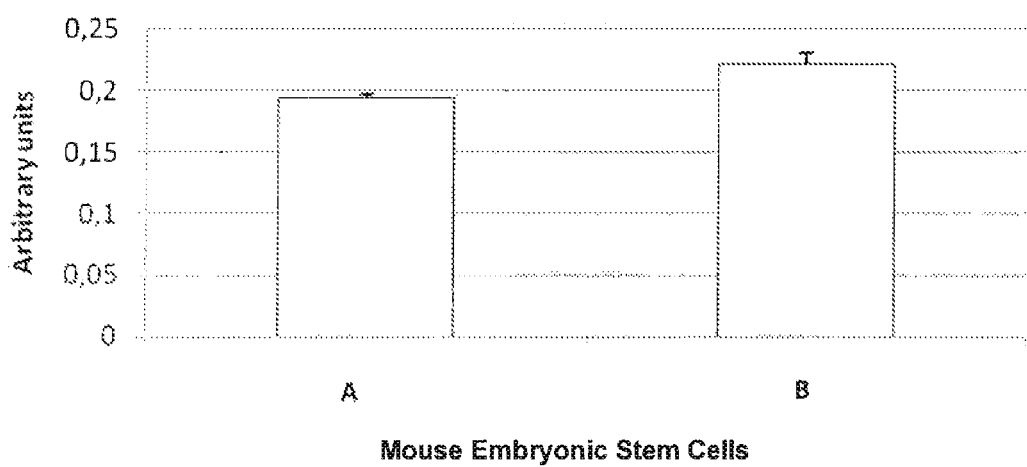
FIG. 4: Viability (Cell Titer-Glo®) 48 h post-thawing for Mouse Embryonic Stem Cells. A: Gold Standard vitrification method. B: Invention's method.

One week later, all cells were quickly thawed in a water bath at 37° C. Thawed cells from both the gold standard and the new vitrification method were gradually diluted by adding 2 ml of DMEM containing 10% FCS and 0.5M trehalose during a period of 6 minutes. Post-thawing cell viability was then checked for all assays using trypan blue (Countess® cell counter, from Invitrogen). Cells were then seeded in 24-well plates at a concentration of 80000 cells per well with complete culture medium and 48 hours later a Cell Titer-Glo® assay (Promega) was performed to measure cellular metabolism. FIG. 3 shows an increase in viability from 65.5% to 85% when using the new vitrification method. FIG. 4 shows a 12.2% increment in the number of viable cells 48 hours after thawing when using the invention's vitrification method.

Example 4

Freezing/Thawing Assay of HEK 293 Cells Using the Gold Standard Freezing Method and the New Freezing Method The cell line HEK 293 was acquired from the Heath Protection Agency (HPA). Cells were cultured in flasks (Nunc, Thermo Scientific) in complete culture medium (DMEM high glucose from Hyclone supplemented with 10% FBS from Gibco, 100 μg/ml penicillin and 100 IU/ml streptomycin from Hyclone), grown in flasks until they were 80% confluent and then harvested. Cell detachment was achieved by incubation with PBS EDTA 4 mM (from Sigma) at 37° C. for 5 minutes. Cells were centrifuged at 450×G for 5 minutes. After supernatant removal, cells were suspended in freezing solution (complete culture medium plus 10% DMSO from Sigma) at 4° C. at a density of 1×10$^6$ cells/ml. Cell densities were determined by using an automatic cell counter (Countess®, Invitrogen). The sample was then split in two parts that followed two different freezing protocols, the gold standard freezing protocol and the new freezing protocol. For the gold standard freezing protocol a total of 0.3 ml of cells were allowed to equilibrate for 10 minutes at 4° C. prior to be frozen down to −80° C. at −1° C./minute in 1.8 ml cryovials (Nunc, Thermo Fisher Scientific). Freezing rates of −1° C./minute were reached by using CoolCell® system (Biocision LLC, California). For the new freezing method, cells were allowed to equilibrate for 5 minutes at 4° C. followed by a centrifugation at 450×G for another 5 minutes. During this centrifugation period, the temperature of the freezing solution started to drop at −1° C./minute until reaching 0° C. Cells were then concentrated at a density of 129 million cells/ml and the resulting 0.3 ml were quickly transferred to the compartment of a special freezing container, having said compartment a surface area to volume ratio of 8.4 cm$^{-1}$. Cells were then frozen down to −80° C. at −1° C./minute along with 1.5 ml of eluting solution (complete cell culture medium) that was placed in a separate compartment within said container. All cells from both freezing methods were transferred the next day from −80° C. to −160° C. (vapour phase of liquid nitrogen).

Cells from both freezing methods were quickly thawed in a water bath at 37° C. one week after freezing. Thawed cells from the gold standard freezing method were gradually diluted at a pace of 1 ml/minute with 1.5 ml of complete culture medium. Cells frozen with the new method were auto-diluted as they were thawing. Post-thawing cell viability was then checked in both assays using trypan blue (Countess® cell counter, from Invitrogen). Cells from both freezing methods were seeded along with fresh cells in T-175 flasks, allowed to grow for 72 hours in a $CO_2$ incubator at 37° C. and then the total number of cells was counted using the Countess® cell counter.

Figure 5:
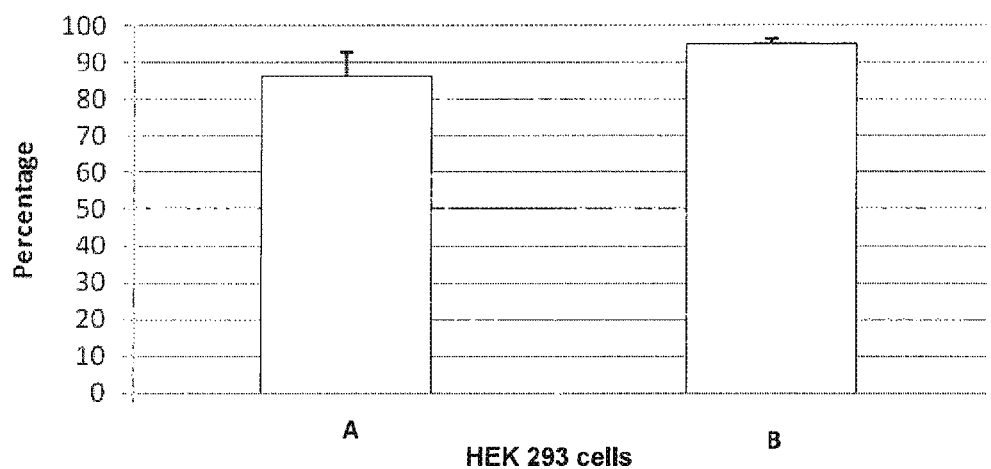
FIG. 5: Post thawing membrane integrity (Trypan Blue) for Human Embryonic Kidney HEK 293 cells. A: Gold Standard method. B: Invention's method.

FIG. 5 shows a higher percentage of viable HEK293 cells in terms of cell membrane integrity after thawing when using the new freezing method (95%) as compared to the gold standard method (86%).

Figure 6:
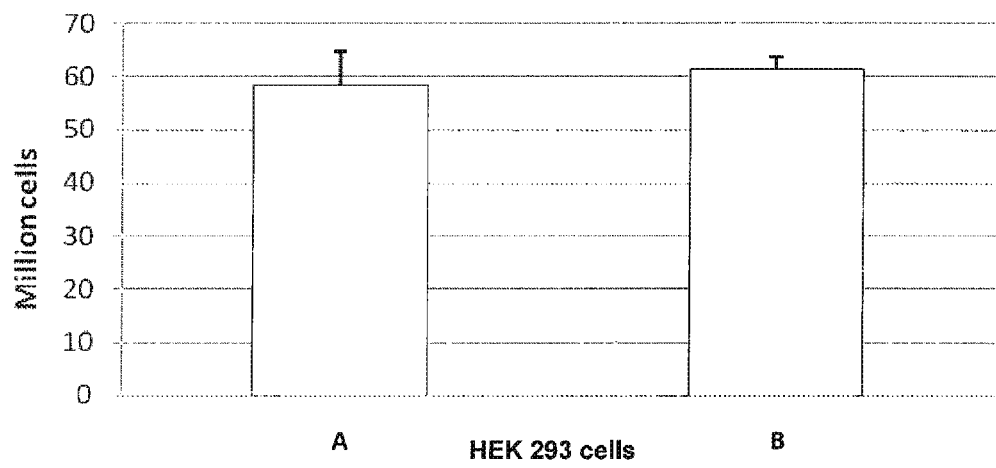
FIG. 6: Total number of HEK 293 cells after 72 h growth. A: Invention's method. B: Fresh cells.

FIG. 6 shows similar growth efficiencies between fresh HEK293 cells in culture and cells frozen/thawed with the new freezing method after 72 hours growth.

Example 5

Freezing/Thawing Assay of MDCK Cells Using the Gold Standard Freezing Method Versus New Freezing Methods The cell line MDCK was acquired from the Heath Protection Agency (HPA). Cells were cultured in T-175 flasks (Nunc, Thermo Scientific) in complete culture medium (MEM, 2 mM L-glutamine from Hyclone, 1% non-essential amino acids from Sigma supplemented with 10% FBS from Gibco, 100 μg/ml penicillin and 100 IU/ml streptomycin from Hyclone), grown until they were 80% confluent and then harvested. Cell detachment was achieved by an initial incubation with PBS EDTA 4 mM at 37° C. for 5 minutes followed by another 5 minute incubation with TrypLE™ Express (Invitrogen). Cells were centrifuged at 450×G for 5 minutes. After supernatant removal, cells were suspended in freezing solution (complete culture medium plus 10% DMSO from Sigma) at 4° C. at a density of 1 million cells/ml and split into three parts. Cell densities were determined by using an automatic cell counter (Countess®, Invitrogen). Each part was then processed for freezing following three different protocols. For the gold standard freezing protocol, a total of 0.3 ml of cells were allowed to equilibrate for 10 minutes at 4° C. prior to be frozen down to −80° C. at −1° C./minute in 1.8 ml cryotubes (Nunc, Thermo Fisher Scientific). Freezing rates of −1° C./minute were reached by using CoolCell® system (Biocision LLC, California). For the other two new freezing methods, a total of $41.5 \times 10^6$ cells were allowed to equilibrate for 5 minutes at 4° C. in 41.5 ml of freezing solution followed by a centrifugation at 450×G for another 5 minutes. During this centrifugation period, the temperature of the freezing solution started to drop at −1° C./minute until reaching 0° C. Cells were then concentrated at a density of $92 \times 10^6$ cells/ml and 0.225 ml of this concentrated freezing solution were quickly transferred to each of the two different containers depending on the freezing method chosen. One of the containers was a 1.8 ml cryotube (Nunc) and the other one was the special freezing container having a cell compartment with a surface area to volume ratio of 8.4 $cm^{-1}$ along with a separate compartment within said container, containing 1.5 ml complete medium as the eluting solution. All freezing containers were then frozen down to −80° C. at −1° C./minute. Cells from all freezing methods were transferred the next day from −80° C. to −160° C. (vapour phase of liquid Nitrogen).

All cells were quickly thawed in a water bath at 37° C. one week after freezing. Thawed cells contained in the two 1.8 ml cryotubes (Nunc) were gradually diluted at a pace of 1 ml/minute with 1.5 ml complete culture medium. Cells frozen within the new freezing container were auto-diluted as they were thawing. Post-thawing cell viability was then checked for all assays using trypan blue (Countess® cell counter, from Invitrogen). Cells from all freezing methods were seeded along with fresh cells in T-175 flasks, allowed to grow for 48 hours in a $CO_2$ incubator at 37° C. and then the total number of cells was counted using the Countess® cell counter.

Figure 7:
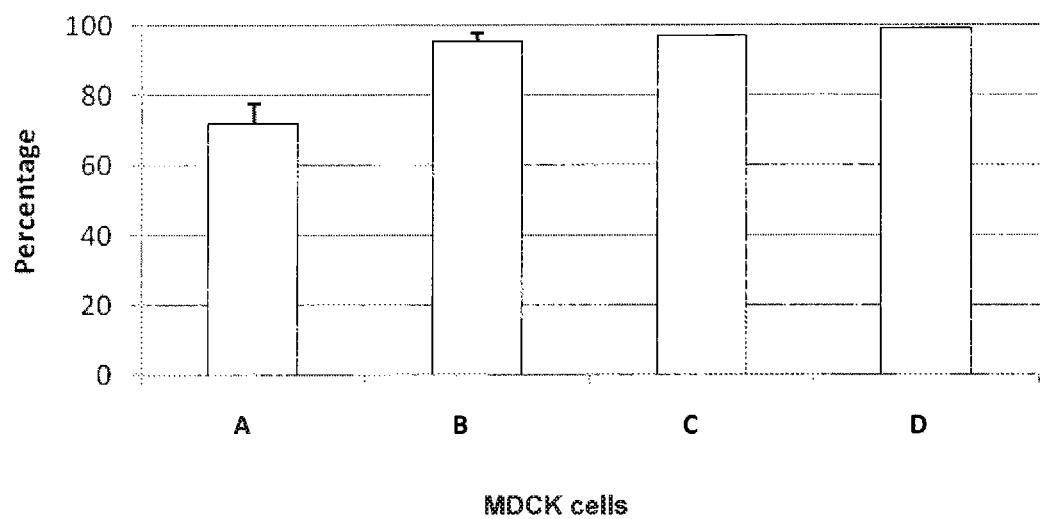
FIG. 7: Post thawing membrane integrity (Trypan Blue) for Madin-Darby Canine Kidney MDCK cells. A: Gold Standard method in cryovial. B: Invention's method in cryovial. C: Invention's method in vial. D: Fresh cells.

FIG. 7 shows just 72% of viable MDCK cells when following the gold standard freezing protocol as compared with the rest of novel freezing methods that are well above 90% viability. This figure also shows that for this particular cell type, the step of cell concentration is the one that accounts for good viability results reaching levels closed to fresh cells (95%, 97% and 99% respectively).

Figure 8:
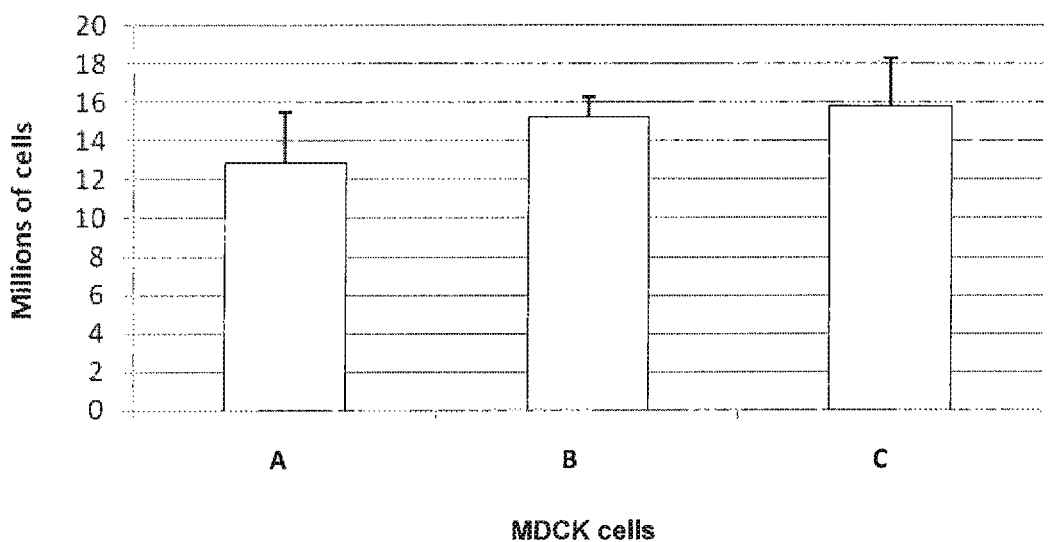
FIG. 8: Total number of cells after 48 h growth for MDCK cells. A: Gold Standard method. B: Invention's method. C: Fresh cells.

FIG. 8 shows a better performance of the new freezing method than the gold standard method in terms of growth efficiency. Cells frozen and thawed with the new method, reach similar total numbers of cells after 48 hours growth when compared to fresh cells (15.25 versus 15.75 million cells respectively).

Example 6

Freezing/Thawing Assay of CHO Cells Using Two Variations of the New Freezing Method The cell line CHO was acquired from the Heath Protection Agency (HPA). Cells were cultured in flasks (Nunc, Thermo Scientific) in complete culture medium (DMEM/Nutrient mixture F12 Ham from Sigma Aldrich, supplemented with 10% FBS from Gibco, 100 μg/ml penicillin and 100 IU/ml streptomycin from Hyclone), grown in flasks until they were 80% confluent and then harvested. Cell detachment was achieved by incubation with 4 mM PBS-EDTA (from Sigma) at 37° C. for 5 minutes. A total of $55 \times 10^6$ cells were centrifuged at 450×G for 5 minutes. After supernatant removal, cells were suspended in freezing solution (complete culture medium plus 10% DMSO from Sigma) at 4° C. at a density of 3 million cells/ml and cells were allowed to equilibrate for 5 minutes at 4° C. Cell densities were determined by using an automatic cell counter (Countess®, Invitrogen). The sample was then split into two identical halves containing the same number of cells. The two samples were then centrifuged at 450×G for 5 minutes at different temperatures. One half was spin down at +20° C. whereas the other half was spin down at 0° C. at a rate of −1° C./minute. Cells from both assays were then concentrated at a density of $68 \times 10^6$ cells/ml and a total of 0.4 ml for each assay were quickly transferred to the cellular compartments of two special freezing containers, having said compartments a surface area to volume ratio of 8.4 $cm^{-1}$. Cells were then frozen down to −80° C. at −1° C./minute along with 0.6 ml of an eluting solution consisting of complete medium that was placed in a separate compartment within said freezing containers. Freezing rates of −1° C./minute were reached by using CoolCell® system (Biocision LLC, California). All cells from both freezing methods were transferred the next day from −80° C. to −160° C. (vapour phase of liquid Nitrogen).

Cells from both freezing methods were quickly thawed in a water bath at 37° C. one week after freezing. Frozen cells within the freezing solution were auto-diluted in the complete medium as they were thawing, contributing to a low osmotic shock. Post-thawing cell viability was then checked in both assays using trypan blue (Countess® cell counter, from Invitrogen). In order to compare the post-thawing cell growth recovery between both protocols, cells from both freezing methods were seeded in different T-175 flasks, allowed to grow for 48 hours in a $CO_2$ incubator at 37° C. and then the total number of cells was counted using the Countess® cell counter.

Figure 9:
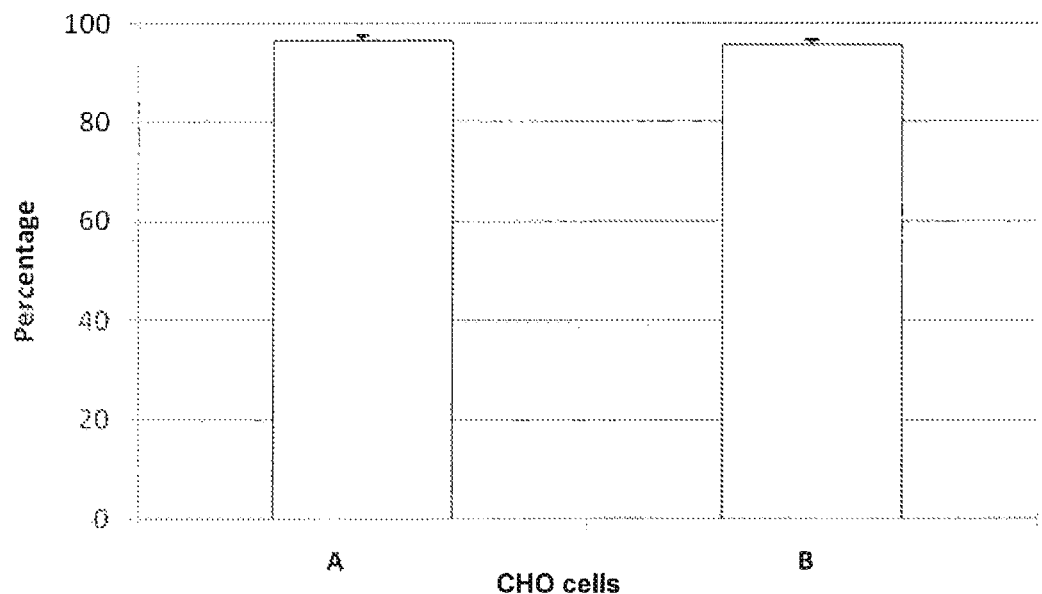
FIG. 9: Post thawing membrane integrity (Trypan Blue) for Chinese Hamster Ovary CHO cells. A: Concentrating step at 0° C. B: Concentrating step at 20° C.

FIG. 9 shows no major cell membrane integrity impact for this particular cell type when concentrating cells at 0° C. or at +20° C. (96.5% versus 95.5% viability respectively).

Figure 10:
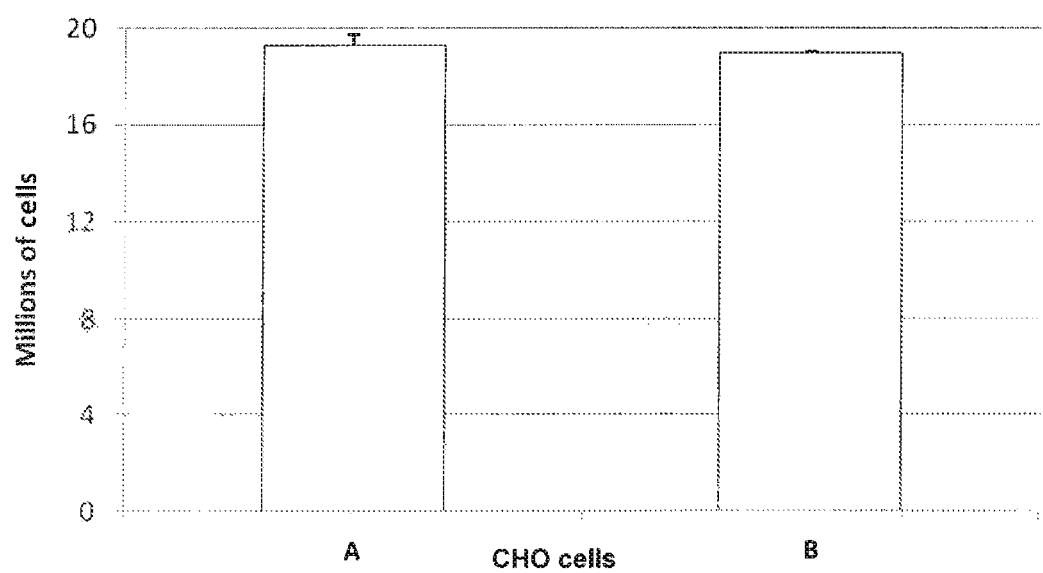
FIG. 10: Total number of CHO cells after 48 h post-thawing. A: Concentrating step at 0° C. B: Concentrating step at 20° C.

FIG. 10 shows no impact in cell growth, when comparing the two different temperatures at which cells were concentrated. Cells concentrated at a $T^a$ of 0° C. reached a total of 19.25×10$^6$ cells after 48 hours in culture whereas cells concentrated at +20° C. reached a total of 18.95×10$^6$ cells.

Example 7

Freezing/Thawing Assay of Dental Pulp Stem Cells Comparing the Use of a Standard Freezing Container Versus the Double Wall Container of the Invention Dental Pulp Stem Cells (DPSC) were isolated from a deciduous tooth of a 6 year old girl. Cells were obtained from explants of the dental pulp, cultured in flasks (Nunc®, Thermo Scientific) in complete culture medium (DMEM high glucose from Hyclone supplemented with 10% FBS from Gibco, 100 µg/ml penicillin, 100 IU/ml streptomycin from Hyclone and 4 µg/ml gentamicin from Sigma) until they were 80% confluent and then harvested. Cell detachment was achieved by incubation with PBS EDTA 4 mM (from Sigma) at 37° C. for 5 minutes. Cells were centrifuged at 450×G for 5 minutes. After supernatant removal, cells were counted and suspended in a total of 2 ml of freezing solution at 4° C. (consisting of complete culture medium plus 10% DMSO from Sigma) at a density of 1×10$^6$ cells/ml. Cell densities were determined by using an automatic cell counter (Countess®, Invitrogen). The cells suspended in 2 ml of freezing solution were then split in two identical parts. One part consisting of one milliliter of cell suspension was placed in a standard cryovial (from Nunc®). The other milliliter was placed in the outer compartment of the special freezing container of the invention, having said compartment a surface area to volume ratio of 20 cm$^{-1}$. The inner compartment of the special freezing container was filled with 2 ml of eluting solution (complete cell culture medium) at 4° C. Both cryovials, the standard from Nunc® and the special freezing container, were then frozen down to −80° C. at −1° C./minute. Freezing rates of −1° C./minute were reached by using CoolCell® system (Biocision LLC, California). All cells from both freezing containers were transferred the next day from −80° C. to −160° C. (vapour phase of liquid nitrogen).

Cells from both freezing containers were quickly thawed in a water bath at 37° C. one week after freezing. Thawed cells from the standard container from Nunc® were gradually diluted at a pace of 1 ml/minute with 2 ml of complete culture medium. Cells frozen in the special container were auto-diluted as they were thawing in an upside down position. Post-thawing cell viability was then checked in both assays using trypan blue (Countess® cell counter, from Invitrogen). Cells from both freezing containers were seeded in two different T-175 flasks and allowed to grow for 48 hours in a CO$_2$ incubator at 37° C. and then the total number of cells was counted using the Countess® cell counter.

Figure 11:
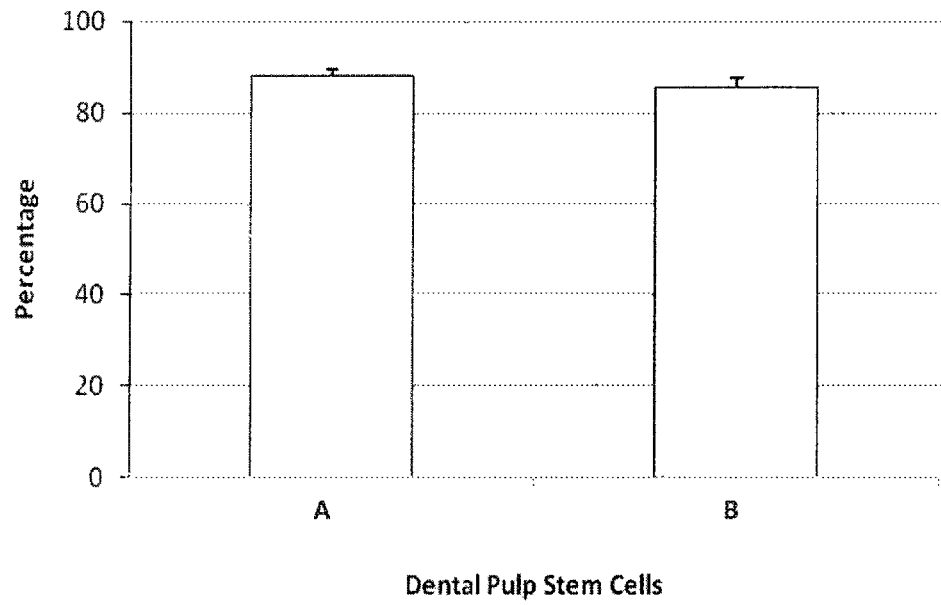
FIG. 11: Post thawing membrane integrity (Trypan Blue) for Dental Pulp Stem Cells. A: Cells frozen in standard cryovial. B: Cells frozen in invention's container.

FIG. 11 shows a similar post thawing percentage of viable DPSC in terms of cell membrane integrity for both containers (88% versus 85.5%).

Figure 12:
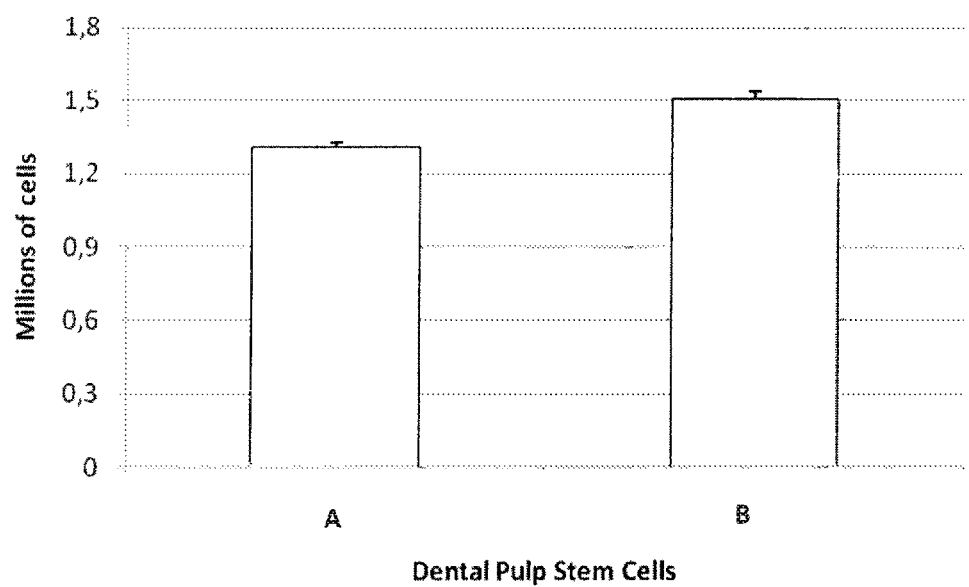
FIG. 12: Total number of Dental Pulp Stem Cells after 48 h growth. A: Cells frozen in standard cryovial. B: Cells frozen in invention's container.

FIG. 12 shows how the total number of cells after 48 h incubation was higher for those cells that were frozen in the novel freezing container (1.5 million cells) than for those cells that were frozen in the standard container (just 1.3 million cells).

The invention claimed is:

1. A container comprising concentrated frozen cells comprising frozen cells with an internalized cryoprotective agent, wherein cryoprotective agent not internalized within the cells has been withdrawn.

2. The container according to claim 1, wherein said container is a bottle with a conical lid, said bottle containing a frozen concentrated pellet of cells in the lid and frozen fresh acceptable eluent.

3. The container according to claim 1, wherein said container is a clamped bag containing the frozen concentrated cells at a lower side of the bag and frozen fresh acceptable eluent at an upper side of the bag.

4. The container according to claim 1, wherein said container comprises a double wall and at least an inner compartment and an outer compartment communicated with each other creating a common space that ends in an opening, wherein the inner compartment is at least partially filled with a frozen fresh biologically acceptable eluent and the outer compartment hosts the frozen concentrated cells, and has a surface-to-volume ratio between 6 and 50 cm$^{-1}$.

5. The container according to claim 4, wherein the volume of said concentrated cells is equal or less than the volume of said liquid eluent.

6. The container according to claim 4, wherein said container is a vial, a flask, or a syringe.

7. The container according to claim 4 wherein said container has a surface-to-volume ratio of between 8 and 21 cm$^{-1}$.

8. The container according to claim 4 wherein said container is a cylinder-shaped container with a circular inner wall.

9. The container according to claim 1, wherein said cryoprotective agent is selected from the group consisting of dimethyl sulphoxide, glycerol, polyvinyl-pyrrolidone, ethylene glycol, methanol, methyl acetamide and sugars, and combinations thereof.

10. The container according to claim 9, wherein said cryoprotective agent is dimethyl sulphoxide.

11. The container according to claim 1, wherein the container has a surface-to-volume ratio between 6 and 50cm$^{-1}$.

12. The container according to claim 1, wherein the container has a surface-to-volume ratio between 8 and 21 cm-1.

13. The container according to claim 1, wherein said cells are bacteria, plant cells or animal cells.

14. The container according to claim 13, wherein said animal cells are selected from the group consisting of blood cells, stem cells, induced pluripotent stem cells, tumor cell lines, immortalized cell lines, continuous cell lines, genetically modified cell lines, hybridomas, primary isolated cells, embryos, sperm and oocytes.

15. The container according to claim 14, wherein said stem cells are selected from the group consisting of embryonic stem cells, adult stem cells, tissue specific stem cells, mesenchymal stem cells, hematopoietic stem cells and progenitor cells.

16. A container comprising an outer wall and an inner wall forming an outer compartment and an inner compartment, wherein the inner wall is lower than the outer wall, the outer and inner compartments communicate with each other creating a common space that ends in an opening, wherein the outer compartment has a surface-to-volume ratio of between 8 and 21 cm$^{-1}$.

17. The container according to claim 16, comprising a removable lid in said opening.

18. The container according to claim 17, wherein said container is a vial or flask.

19. A method of freezing cells, comprising the steps of:
(a) incubating the cells in a solution comprising a cyroprotective agent, whereby the cryoprotective agent is internalized within the cells;
(b) concentrating the cells resulting from step (a) by withdrawing cryoprotective agent that has not been internalized within the cells; and
(c) freezing the concentrated cells resulting from step (b) in a container.

20. The method according to claim 19, wherein the incubating step (a) is performed at a temperature of 3 to 5° C.

21. The method according to claim 19, wherein the cryoprotective agent is selected from the group consisting of dimethyl sulphoxide, glycerol, polyvinyl-pyrrolidone, ethylene glycol, methanol, methyl acetamide and sugars, and combinations thereof.

22. The method according to claim 21, wherein the cryoprotective agent is dimethyl sulphoxide.

23. The method according to claim 19, wherein the concentrating step (b) is performed at a temperature cooling gradient of 1 to 2° C./min.

24. The method according to claim 19, wherein the concentrating step (b) is performed by centrifugation or filtration.

25. The method according to claim 19, wherein the freezing step (c) is performed at a temperature cooling gradient of 1 to 2° C./min.

26. The method according to claim 19, wherein the freezing step (c) is performed by vitrification.

27. The method according to claim 19, wherein the freezing step (c) is performed in a container having a surface-to-volume ratio between 6 and 50 $cm^{-1}$.

28. The method according to claim 27, wherein the ratio is between 8 and 21 $cm^{-1}$.

29. The method according to claim 19, wherein said cells are bacteria, plant cells or animal cells.

30. The method according to claim 29, wherein the animal cells are selected from the group consisting of blood cells, stem cells, induced pluripotent stem cells, tumor cell lines, immortalized cell lines, continuous cell lines, genetically modified cell lines, hybridomas, primary isolated cells, embryos, sperm and oocytes.

31. The method according to claim 30, wherein the stem cells are selected from the group consisting of embryonic stem cells, adult stem cells, tissue specific stem cells, mesenchymal stem cells, hematopoietic stem cells and progenitor cells.

* * * * *